United States Patent
Bergonzelli Degonda et al.

(10) Patent No.: US 9,034,314 B2
(45) Date of Patent: May 19, 2015

(54) NUTRITIONAL COMPOSITION COMPRISING PROBIOTICS AND IMPROVING SLEEP PATTERNS

(75) Inventors: Gabriela Bergonzelli Degonda, Bussigny (CH); Isabelle Bureau-Franz, Epalinges (CH); Clara Lucia Garcia-Rodenas, Forel (CH)

(73) Assignee: Nestec S.A., Vevey (CH)

( * ) Notice: Subject to any disclaimer, the term of this patent is extended or adjusted under 35 U.S.C. 154(b) by 86 days.

(21) Appl. No.: 13/127,164

(22) PCT Filed: Oct. 29, 2009

(86) PCT No.: PCT/EP2009/064276
§ 371 (c)(1),
(2), (4) Date: May 2, 2011

(87) PCT Pub. No.: WO2010/060722
PCT Pub. Date: Jun. 3, 2010

(65) Prior Publication Data
US 2011/0206649 A1    Aug. 25, 2011

(30) Foreign Application Priority Data
Nov. 3, 2008 (EP) .................................. 08168161

(51) Int. Cl.
*A23L 1/30* (2006.01)
*A61K 31/00* (2006.01)

(52) U.S. Cl.
CPC .............. *A61K 35/742* (2013.01); *A23L 1/3014* (2013.01); *A23V 2002/00* (2013.01); *A61K 31/00* (2013.01); *A61K 35/744* (2013.01); *A61K 35/747* (2013.01); *A61K 35/745* (2013.01)

(58) Field of Classification Search
None
See application file for complete search history.

(56) References Cited

U.S. PATENT DOCUMENTS

| 6,444,203 | B2 * | 9/2002 | Krueger et al. | 424/93.44 |
| 7,374,924 | B2 * | 5/2008 | Connolly et al. | 435/252.9 |
| 2008/0176305 | A1 | 7/2008 | Sato et al. | |
| 2008/0206212 | A1 * | 8/2008 | McMahon et al. | 424/93.45 |

FOREIGN PATENT DOCUMENTS

| EP | 2110028 | 10/2009 |
| JP | 2006062998 | 3/2006 |
| JP | 2006160697 | 6/2006 |
| JP | 2007143479 | 6/2007 |
| JP | 2008137941 | 6/2008 |
| UA | 28995 | 12/2007 |
| WO | WO 96/11014 | 4/1996 |
| WO | WO 01/45722 | 6/2001 |
| WO | WO 02/07741 | 1/2002 |
| WO | 2007093619 | 8/2007 |
| WO | WO 2007/142596 | 12/2007 |

OTHER PUBLICATIONS

Davenne et al., Am J Physiol Regulatory Integrative Comp. Physiol., vol. 253, pp. R646-R654, 1987.*
Chen et al., Hu Li Za Zhi, 2006, English Abstract.*
Chen et al., Hu Li Za Zhi, 2006, vol. 53, Issue No. 4, pp. 17-23; English translation, pp. 1-27.*
Folster-Holst, et al., "Prospective, randomized controlled trial on *Lactobacillus rhamnosus* in infants with moderate to severe atopic dermatitis," British Journal of Dermatology, vol. 155, No. 6, Dec. 2006, pp. 1256-1261, XP002534276.
Logan, et al., "Major depressive disorder: probiotics may be an adjuvant therapy," Medical Hypotheses, vol. 64, No. 3, 2005, pp. 533-538, XP002534278.
Brown, et al., "Autochthonous Intestinal Bacteria and Coprophagy: A Possible Contribution to the Ontogeny and Rhythmicity of Slow Wave Sleep in Mammals," Medical Hypotheses, vol. 26, No. 3, 1998, pp. 171-176, XP002534277.
Ono, et al., "A Pilot Study of the Relationship between Bowel Habits and Sleep Health by Actigraphy Measurement and Fecal Flora Analysis," Journal of Physiological Anthropology, May 2008, vol. 27, No. 3, pp. 145-151, XP008107644.
Pollmacher, et al., "Influence of host defense activation on sleep in humans," Advances in Neuroimmunology, vol. 5, No. 2, 1995, pp. 155-169, XP002573006.
France, et al., "Infant sleep disturbance: Description of a problem behaviour process," Sleep Medicine Reviews, vol. 3, No. 4, 1999, pp. 265-280.
Field, et al., "Sleep disturbances in depressed pregnant women and their newborns," Infant Behavior & Development, vol. 30, 2007, pp. 127-133.
Kushikata, et al., "Brain-deprived neurotrophic factor enhances spontaneous sleep in rats and rabbits," American Physiological Society, No. 5, 1999, pp. R1334-R1338.
Faraguna, et al., "A Causal Role for Brain-Derived Neurotrophic Factor in the Homeostatic Regulation of Sleep," The Journal of Neuroscience, Apr. 2008, vol. 28, No. 5, pp. 4088-4095.
Salminen, et el., "Probiotics: how should they be defined?" Trends in Food Science & Technology, vol. 10, 1999, pp. 107-110.
Duman, et al., "Neuronal Plasticity and Survival in Mood Disorders," Biol. Psychiatry, vol. 48, 2000, pp. 732-739.

(Continued)

*Primary Examiner* — Allison Fox
*Assistant Examiner* — Yvonne Pyla
(74) *Attorney, Agent, or Firm* — K&L Gates LLP

(57) ABSTRACT

This invention relates to the use of a probiotic bacterial strain in the manufacture of a medicament or therapeutic nutritional composition for improving the maturation of sleep patterns in infants, young children or young animals and/or for reducing sleep disturbances and/or improving sleep patterns in humans or animals at any age.

24 Claims, 2 Drawing Sheets

(56) References Cited

OTHER PUBLICATIONS

Espiritu, et al., "Aging-Related Sleep Changes," Clinics in Geriatric Medicine, vol. 24, 2008, pp. 1-14.

Chorney, et al., "The Interplay of Sleep Disturbance, Anxiety, and Depression in Children," Journal of Pediatric Psychology, vol. 33, No. 4, 2008, pp. 339-349.

LeBlanc, et al., Incidence and Risk Factors of Insomnia in a Population-Based Sample, Sleep, vol. 32, No. 8, 2009, pp. 1027-1037.

Tapia-Arancibia, et al., "New insights into brain BDNF function in normal aging and Alzheimer disease," Brain Research Reviews, vol. 59, 2008, pp. 201-220.

International Search Report for International Application No. PCT/EP2009/064276 mailed on Mar. 24, 2009.

Written Opinion for International Application No. PCT/EP2009/064276 mailed on Mar. 24, 2009.

Simpson et al. "Sleep and Inflammation" Nutrition Reviews, vol. 65, No. 12, Dec. 2007, pp. S244-S252.

\* cited by examiner

Fig. 1

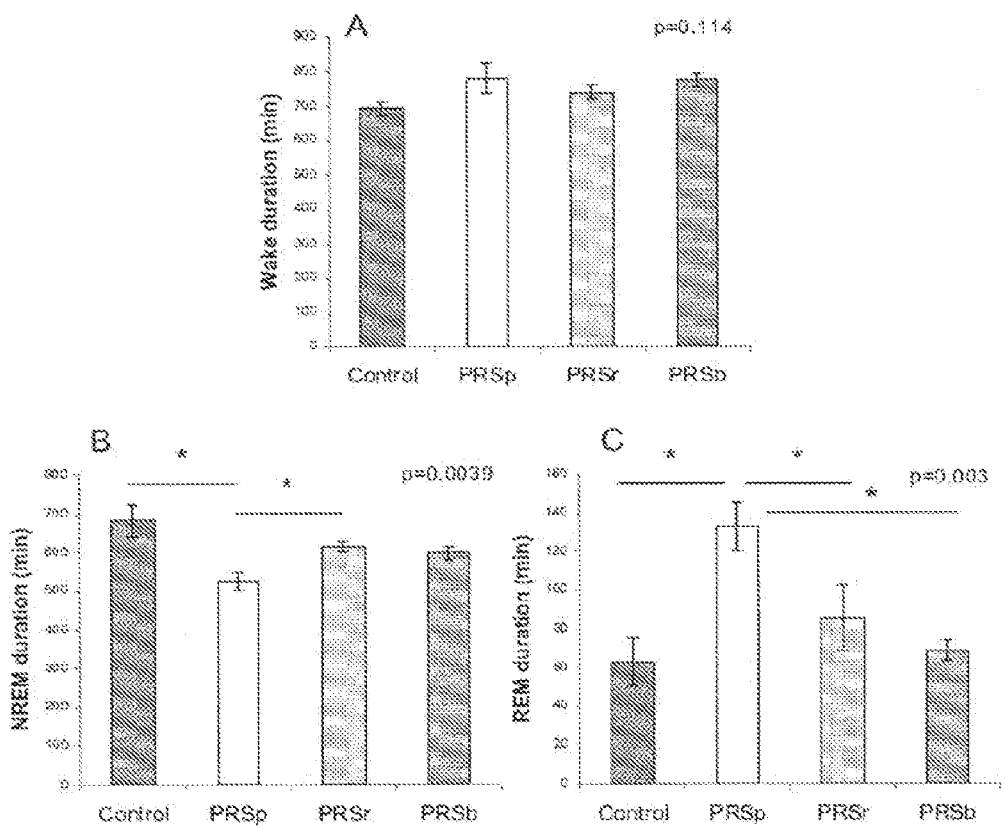

Fig. 1. Total duration (minutes) of wake (A), NREM (B) and REM (C) states during the 24 hour polygraphic recording period in control or prenatal stress (PRS) animals. Animals received a daily gavage of either placebo (Control and PRSp), *L. reuteri* DSM 17938 (PRSr) of *B. longum* ATCC BAA-999 (PRSb) during the 14 days preceding polygraphic recordings. Average ± SEM data, as well as the p value for the global group effect (one-way ANOVA test) are shown. The symbol * between two bars indicates a significant difference ($p<0.05$) between the two groups (Tukey-Kramer Multiple-Comparison Test)

Fig. 2

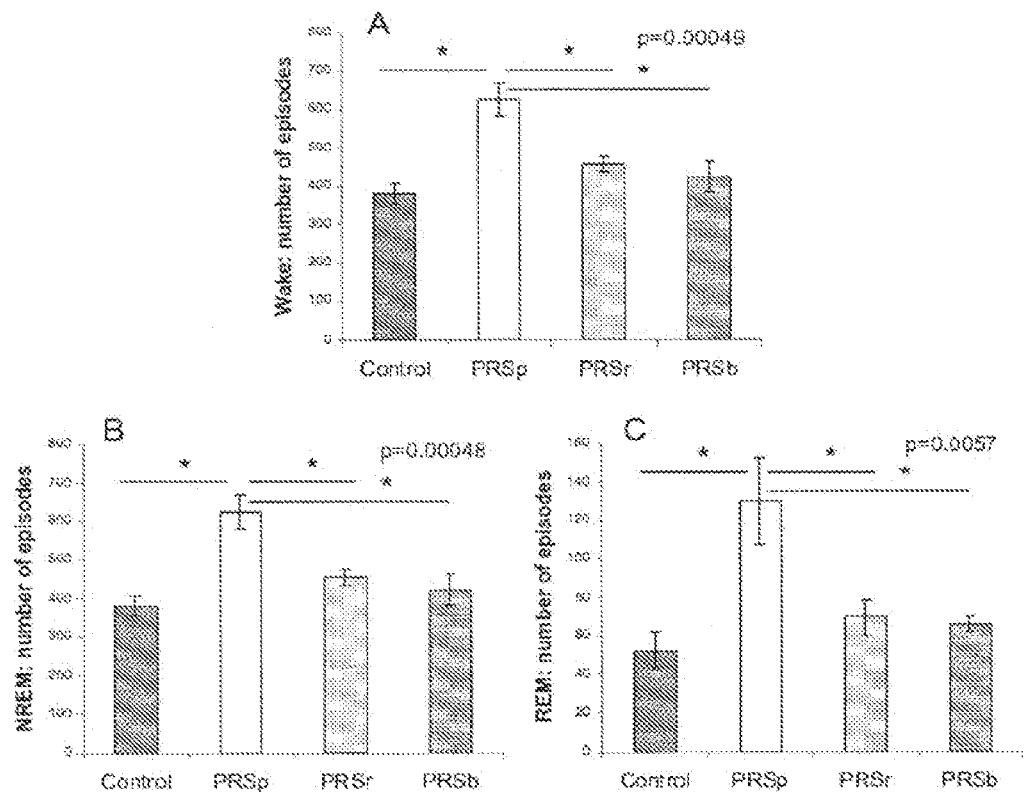

Fig. 2. Number of episodes of wake (A), NREM (B) and REM (C) states during the 24 hour polygraphic recording period in control or prenatal stress (PRS) animals. Animals received a daily gavage of either placebo (Control and PRSp), *L. reuteri* DSM 17938 (PRSr) of *B. longum* ATCC BAA-999 (PRSb) during the 14 days preceding polygraphic recordings. Average ± SEM data, as well as the p value for the global group effect (one-way ANOVA test) are shown. The symbol * between two bars indicates a significant difference ($p<0.05$) between the two groups (Tukey-Kramer Multiple-Comparison Test)

NUTRITIONAL COMPOSITION COMPRISING PROBIOTICS AND IMPROVING SLEEP PATTERNS

FIELD OF THE INVENTION

This invention relates to the use of probiotic bacterial strains to improve the maturation of sleep patterns and reduce night wakefulness in infants and young children and/or to reduce sleep disturbances and improve sleep quality in humans or animals suffering from sleep alterations at any age.

BACKGROUND OF THE INVENTION

Sleep disturbances are observed at any stage of the life. These disturbances are typically characterized by a decrease in the ability to initiate and maintain sleep, and by a reduced proportion of the deeper, more restorative sleep. Quality of life is substantially impaired in individuals suffering from those alterations.

Infant sleep normally changes over the first months of life to follow a diurnal rhythm with sleep lasting for a long unbroken period at night and, similarly, sleep states change from being equally distributed between REM (active) and NREM (quiet) sleep at birth to one third REM and two thirds NREM by 8 months of age. Any failure to successfully negotiate these changes in infancy can also have lasting effects on the sleep patterns of the child.

The most common sleep disturbances in infants and children are those related to wakefulness (i.e. either difficulties in settling at bedtime or failure to sleep through the night without interruptions). It has been estimated that these disturbances affect 15 to 35% of infants aged less than 24 months (France et al, "Infant Sleep Disturbance: Description of a problem behaviour process", Sleep Medicine Reviews, Vol 3, No 4, pp 265-280, 1999). Infant and child sleep disturbances inevitably lead to parental sleep disturbance and stress which may result in inadequate child-parent interaction which in turn aggravates infant and child symptoms leading to a vicious circle.

Much of the literature which deals with infant sleep disturbance focuses on psychological factors such as pre- and post-natal stress and high levels of anxiety in the mother. For example, Field and co-workers studied the relationship between sleep disturbance, depression, anxiety and anger in pregnant women in the second and third trimesters of pregnancy and sleep patterns of their new-born infants. They observed that infants born to depressed mothers also suffered from sleep disturbances including less time in deep sleep and more time in indeterminate (disorganised) sleep (Field et al, "sleep disturbances in depressed pregnant women and their newborns", Infant Behavior and Development 30 (2007) 127-133).

These and similar observations have led paediatricians when consulted by parents of infants and children about infant sleep disturbance to focus on recommending behavioural management techniques, such as establishing a consistent bedtime ritual, moving gradually bedtime to an earlier time or gradually reducing attention given on waking. These measures can be effective but are often difficult for the parents to apply.

Normal aging is accompanied by changes in the sleep quality, quantity, and architecture. Specifically, there appears to be a measurable decrease in the ability of the healthy elderly to initiate and maintain sleep, accompanied by a decrease in the proportion of the deeper, more restorative NREM sleep (Espiritu J R. Aging-related sleep changes, Clin Geriatr Med. 2008 24(1):1-14)

Acute and chronic stress, anxiety and depression typically lead to alterations in sleep patterns and insomnia at any age (Chorney D B, Detweiler M F, Morris T L, Kuhn B R, The interplay of sleep disturbance, anxiety, and depression in children, J Pediatr Psychol. 2008 33(4):339-48; LeBlanc M, Mérette C, Savard J, Ivers H, Baillargeon L, Morin C M, Incidence and risk factors of insomnia in a population-based sample. Sleep. 2009 32(8):1027-37).

Occasionally and in extreme cases, anxiolytic drugs (e.g. benzodiazepin) may be prescribed. However, the efficiency of these drugs is variable, establishment of the correct dose difficult to reach and the risk of adverse side-effects is high. In any event, there is a general reluctance to prescribe powerful medicaments of this type, specially for infants and young children.

From the foregoing, it may be seen that there remains a need for alternative methods to reduce sleep disturbances and improve sleep patterns in different phases of the life.

SUMMARY OF THE INVENTION

The present inventors have surprisingly found that administration of a probiotic bacterial strain may improve sleep quality and reduce the number of episodes of wakefulness in individuals suffering from sleep alterations and/or insomnia and, specifically, induce a more mature sleep pattern in infants and young children. Thus, in an animal model mimicking the sleep alterations experienced by infants and children with poor or immature sleep quality and by adults suffering sleep alterations, the administration of probiotics completely normalized sleep patterns by decreasing the time of active sleep (REM), increasing the time of quiet sleep (NREM) and reducing the number of wake up episodes.

Accordingly, the present invention provides the use of a probiotic bacterial strain in the manufacture of a medicament or therapeutic nutritional composition for inducing a more mature sleep pattern in infants and young children and for reducing sleep disturbance and/or improving sleep patterns at any age. "More mature" is herewith referring to sleep pattern similar to or close to the sleep patterns of subjects not suffering of delayed maturation of the sleep cycle and, in consequence, not suffering from sleep disturbances. "More mature sleep pattern" is characterized by sleep lasting for long unbroken period(s) at night, which is associated to a reduction in the duration of active (REM) sleep and an increase in the duration of quiet (NREM) sleep. Such REM and NREM are good indicators of sleep pattern maturation.

The invention extends to a method of inducing a more mature sleep pattern in infants and young children and for reducing sleep disturbance and/or improving sleep patterns at any age comprising administering to an individual in need thereof a therapeutic amount of a probiotic bacterial strain.

BDNF (Brain-derived neurotrophic factor) is a protein that promotes the survival of neuronal populations located either in the central nervous system or directly connected to the central nervous system. It is a member of a unique family of 15 polypeptide growth factors that influence proliferation, differentiation, survival and death of neuronal and non-neuronal cells. BDNF and the other neurotrophic growth factors, e.g., NGF (nerve growth factor), NT-3 (neurotrophin-3), and NT-4 (neurotrophin-4) are essential for the health and well-being of the nervous system, and mediate higher-order activities such as learning, memory, behaviour in addition to their role in cell survival. It has already been demonstrated that high BDNF levels in the brain enhance spontaneous sleep and NREM duration in animal models (Kushikata, Am J Physiol, 1999) whereas blockage of the TrkB receptors of BDNF lead to perturbations in the sleep patterns (Faraguna et al, J Neurosci, 2008). From unpublished data, the present inventors were aware that a probiotic bacterial strain, namely *Bifidobacterium longum* NCC3001 (ATCC BAA-999, initially provided by Morinaga Milk Industry Co. Ltd. as BB536), increases hippocampal BDNF expression.

Stress, anxiety and depression have been shown to be associated to low BDNF levels in the hippocampus (Duman R S, Malberg J, Nakagawa S, D'Sa C. Neuronal plasticity and survival in mood disorders. Biol Psychiatry. 2000; 48:732-739). Decreased BDNF and/or the expression of its receptors (TrkB.FL, TrkB.T1 and TrkB.T2) have been also described during normal aging (Tapia-Arancibia L, Aliaga E, Silhol M, Arancibia S. Brain Res Rev. 2008, 59(1):201-20). In infants, many physiological processes are not fully mature at birth and only become mature in the first months or years following birth. It is possible that some infants and children may experience low levels of BDNF. Low levels of BDNF in these situations may be responsible for disturbed sleep and/or, in the specific case of infants and children, a failure to develop mature diurnal sleeping patterns. Without wishing to be bound by theory, the present inventors believe that the beneficial effect of administration of a probiotic bacterial strain upon sleep disturbance and sleep patterns may be explained in this way. In other words, administration of an agent which is capable of increasing hippocampal BDNF expression such as a probiotic bacterial strain may thus result in the observed normalization of sleep quality and/or improvement in development of mature sleeping patterns.

DETAILED DESCRIPTION OF THE INVENTION

In this specification, the following terms have the following meanings:—

"infant" means a child under the age of 12 months;

"probiotic" means microbial cell preparations or components of microbial cells with a beneficial effect on the health or well-being of the host. (Salminen S, Ouwehand A. Benno Y. et al "Probiotics: how should they be defined" Trends Food Sci. Technol. 1999:10 107-10);

"sleep disturbed infant/young child" means an infant or young child who awakens in the night and cannot settle back to sleep without the parents being aware of the awakening and/or an infant or young child who cannot self-initiate sleep;

"young child" means a child between the age of one and three years.

All percentages are by weight unless otherwise stated.

The probiotic bacterial strain may be administered as a medicament, for example as a daily dose equivalent to 10e10 cfu dissolved in water and administered on a spoon. Alternatively, the composition of the present invention may be a food product, a nutritional composition, a nutraceutical, a drink, a food additive or an animal food product containing an amount equivalent to between 10e3 and 10e12 cfu/g (dry weight basis), more preferably between 10e6 and 10e9 cfu/g.

For example, the composition may be a human milk fortifier, an infant formula, a follow on formula, a growing up milk, an infant cereal, a baby food, a yogurt, a cereal bar, a breakfast cereal, a dessert, a frozen food, a soup, an animal food, a liquid suspension, a powder, a tablet, a gum, a candy, a nutritional composition and/supplements that are targeted at supporting particular pathological (or undesired physiological conditions or physio-pathological conditions) conditions such as allergies or intolerances, malnutrition, inflammation, critical illness, colics, trauma, infection, surgery, attention deficit/hyperactivity disorders, depression, anxiety, fatigue, or stress and the like, especially when the particular pathological conditions induce disturbances in sleep pattern.

The expression "amount equivalent to" includes the possibilities that the bacteria are live, inactivated or dead or even present as fragments such as DNA or cell wall materials or probiotic metabolites. In other words, the quantity of bacteria is expressed in terms of the colony forming ability of that quantity of bacteria as if all the bacteria were live irrespective of whether only the bacteria metabolites are provided or the bacteria are, in fact, live, inactivated or dead, fragmented or a mixture of any or all of these states.

The probiotic bacterial strain may be a *lactobacillus* or a *bifidobacterium*. Examples of preferred *lactobacillus* species are *Lactobacillus rhamnosus*, *Lactobacillus paracasei* and *Lactobacillus reuteri*. Particularly preferred strains are *Lactobacillus rhamnosus* ATCC 53103, *Lactobacillus rhamnosus* CGMCC 1.3724, *Lactobacillus reuteri* ATCC 55730 and *Lactobacillus reuteri* DSM 17938. Examples of preferred *bifidobacterium* species are *Bifidobacterium lactis*, *Bifidobacterium longum*, *Bifidobacterium breve* and *Bifidobacterium infantis*. Particularly preferred strains include *Bifidobacterium* lactis CNCM I-3446 sold inter alia by the Christian Hansen company of Denmark under the trade mark Bb12, *Bifidobacterium longum* NCC3001, ATCC BAA-999 sold by Morinaga Milk Industry Co. Ltd. of Japan under the trade mark BB536, the strain of *Bifidobacterium breve* sold by Danisco under the trade mark Bb-03, the strain of *Bifidobacterium breve* sold by Morinaga under the trade mark M-16V, the strain of *Bifidobacterium breve* sold by Institut Rosell (Lallemand) under the trade mark R0070 and the strain of *Bifidobacterium infantis* sold by Procter & Gamble Co. under the trade mark *B. infantis*. The probiotics can be selected from the list comprising: the genera Bifidobacteria, Lactobacilli, Lactococci, Enterococci, Streptococci, Propionibacteria, Pediococci, *Escherichia coli*, Debaryomyces, Kluyveromyces, Saccharoymces, Schizosaccharomyces, Zygosaccharomyces, Yarrowia, Candida, the species *Bifidobacterium longum, Bifidobacterium lactis, Bifidobacterium animalis, Bifidobacterium breve, Bifidobacterium infantis, Bifidobacterium bifidum, Bifidobacterium adolescentis, Lactobacillus acidophilus, Lactobacillus helveticus, Lactobacillus casei, Lactobacillus paracasei, Lactobacillus salivarius, Lactobacillus plantarum, Lactobacillus fermentum, Lactobacillus johnsonii, Lactobacillus reuteri, Lactobacillus gasseri, Lactobacillus rhamnosus, Lactococcus* ssp, such as *Lactococcus lactis, Lactococcus cremoris, Lactococcus diacetylactis, Enterococcus faecium, Enterococcus faecalis, Saccharomyces cerevisiae, Saccharomyces boulardii, Schizosaccharomyces pombe, Kluyveromyces lactis, Yarrowia lypolitica* or mixtures thereof, preferably selected from the group consisting of *Lactobacillus johnsonii* (NCC533; CNCM 1-1225), *Bifidobacterium longum* (NCC490; CNCM 1-2170), *Bifidobacterium longum* (NCC2705; CNCM 1-2618), *Bifidobacterium longum* (NCC3001; ATCC BAA-999), *Bifidobacterium lactis* (NCC2818; CNCM 1-3446), *Bifidobacterium breve* (strain A), *Lactobacillus paracasei* (NCC2461; CNCM 1-2116), *Lactobacillus rhamnosus* GG (ATCC53103), *Lactobacillus rhamnosus* LPR(NCC4007; CGMCC 1.3724), *Lactobacillus reuteri* (ATCC 55730), *Lactobacillus reuteri* (DSM 17938), *Enterococcus faecium* SF 68 (NCIMB 10415), *Saccharomices boulardii*, and mixtures thereof.)

The selected probiotic bacterial strain may be cultured according to any suitable method known in the art and prepared for addition to the medicament or nutritional composition of the invention by freeze-drying or spray-drying for example. Alternatively, bacterial strains can be bought from specialist suppliers such as Christian Hansen and Morinaga already prepared in a suitable form for addition to nutritional compositions such as infant formula A suitable daily dose of the probiotic bacteria is from 10e3 to 10e12 colony forming units (cfu), more preferably from 10e7 to 10e11 cfu.

The invention is particularly suitable for induce a more mature sleep pattern in infants and thus improve their sleep quality and reduce the episodes of wakefulness. In one embodiment the invention relates for educing sleep disturbance and/or improving sleep patterns in infants or young animals.

If this age group is to be addressed, the therapeutic nutritional composition is preferably an infant formula or a follow-up formula or the corresponding product for pets or animals.

In one embodiment the improvement of sleep quality or pattern is characterized, comprised or is limited to the reduction of the number of episodes of wake states and/or the reduction of sleep fragmentation and/or the increase of the duration of wake states (indicator of better, less fragmented sleep/awake pattern).

In one embodiment the improvement of sleep quality is characterized by longer nights without being unwillingly awake and by a more peaceful sleep.

In one embodiment the improvement of sleep quality is characterized by better ability to fall asleep.

In one embodiment the sleep quality is improved in subject suffering from disturbed sleep pattern, such as fragmented sleep, nightmares or insomnia.

The general composition of an infant formula for use according to the present invention will now be described by way of example. The infant formula may contain a protein source in an amount of not more than 4.0, 3.0 or 2.0 g/100 kcal, preferably 1.8 to 2.0 g/100 kcal. The type of protein is not believed to be critical to the present invention provided that the minimum requirements for essential amino acid content are met and satisfactory growth is ensured although it is preferred that over 50% by weight of the protein source is whey. In one embodiment the protein content is between 30% and 80% whey proteins. Thus, protein sources based on whey, casein and mixtures thereof may be used as well as protein sources based on soy. As far as whey proteins are concerned, the protein source may be based on acid whey or sweet whey or mixtures thereof and may include alpha-lactalbumin and beta-lactoglobulin in whatever proportions are desired.

The proteins may be intact or hydrolysed or a mixture of intact and hydrolysed proteins. It may be desirable to supply partially hydrolysed proteins (degree of hydrolysis between 2 and 20%), for example for infants believed to be at risk of developing cows' milk allergy. If hydrolysed proteins are required, the hydrolysis process may be carried out as desired and as is known in the art. For example, a whey protein hydrolysate may be prepared by enzymatically hydrolysing the whey fraction in one or more steps. If the whey fraction used as the starting material is substantially lactose free, it is found that the protein suffers much less lysine blockage during the hydrolysis process. This enables the extent of lysine blockage to be reduced from about 15% by weight of total lysine to less than about 10% by weight of lysine; for example about 7% by weight of lysine which greatly improves the nutritional quality of the protein source.

The infant formula may contain a carbohydrate source. Any carbohydrate source conventionally found in infant formulae such as lactose, saccharose, maltodextrin, starch and mixtures thereof may be used although the preferred source of carbohydrates is lactose. Preferably the carbohydrate sources contribute between 35% and 65% of the total energy of the formula. In one preferred embodiment of the invention the carbohydrates comprise rice carbohydrates. In one embodiment at least 5% at least 10%, at least 25% or at least 50%, at least 70%, at least 90%, or about 100% of the carbohydrates (w/w) are rice carbohydrates. It has been shown, in the context of the present invention, that a minimal proportion of rice carbohydrates (at least 10% w/w of the total carbohydrates) can bring a substantial benefit in the sleep pattern. The higher the content in rice carbohydrates, the higher the improvement may be. The effect can be hypothesized to being both related to the presence of starch (in the rice carbohydrates), to the particular nature of the rice carbohydrates, and/or to the additional compounds (in addition to starch) comprised in the rice carbohydrates. Such nutritional composition of the invention comprising rice carbohydrates can be of particular use in the context of infant formula, follow-up formula or food intended for children, young children or infants and especially for those having disturbances of sleep pattern (for example due to colics) and more particularly for infants between 0 and 12 months.

The infant formula may contain a source of lipids. The lipid source may be any lipid or fat which is suitable for use in infant formulas. Preferred fat sources include palm olein, high oleic sunflower oil and high oleic safflower oil. The essential fatty acids linoleic and α-linolenic acid may also be added as may small amounts of oils containing high quantities of preformed arachidonic acid and docosahexaenoic acid such as fish oils or microbial oils. In total, the fat content is preferably such as to contribute between 30 to 55% of the total energy of the formula. The fat source preferably has a ratio of n-6 to n-3 fatty acids of about 5:1 to about 15:1; for example about 8:1 to about 10:1.

An infant formula according to the invention preferably further contains at least one prebiotic in an amount of 0.3 to 10%. A prebiotic is a non-digestible food ingredient that beneficially affects the host by selectively stimulating the growth and/or activity of one or a limited number of bacteria in the colon, and thus improves host health. Such ingredients are non-digestible in the sense that they are not broken down and absorbed in the stomach or small intestine and thus pass intact to the colon where they are selectively fermented by the beneficial bacteria. Examples of prebiotics include certain oligosaccharides, such as fructooligosaccharides (FOS), cow milk oligosaccharides (CMOS) and galactooligosaccharides (GOS). A combination of prebiotics may be used such as 90% GOS with 10% short chain fructo-oligosaccharides such as the product sold under the trade mark RAFTILOSE® or 10% inulin such as the product sold under the trade mark RAFTILINE®. Other examples of prebiotics that can be used in the context of the present invention include the group of oligosaccharides obtained from milk or other sources, optionally containing sialic acid, fructose, fucose, galactose or mannose; Preferred prebiotics are sialo-oligosaccharides (SOS), fructo-oligosaccharides (FOS), galacto-oligosaccharides (GOS), isomalto-oligosaccharides (IMO), xylo-oligosaccharides (XOS), arabino-xylo oligosaccharides (AXOS), mannan oligosaccharides (MOS), oligosaccharides of soy, glycosylsucrose (GS), lactosucrose (LS), sialyl-lactose (SL), Fucosyl-lactose (FL), Lacto-N-Neotetraose (LNNT), lactulose (LA), palatinose-oligosaccharides (PAO), malto-oligosaccharides, gums and/or hydrolysates thereof, pectins, starches, and/or hydrolysates thereof.

The infant formula may also contain all vitamins and minerals understood to be essential in the daily diet and in nutritionally significant amounts. Minimum requirements have been established for certain vitamins and minerals. Examples of minerals, vitamins and other nutrients optionally present in the infant formula include vitamin A, vitamin B1, vitamin B2, vitamin B6, vitamin B12, vitamin E, vitamin K, vitamin C, vitamin D, folic acid, inositol, niacin, biotin, pantothenic acid, choline, calcium, phosphorous, iodine, iron, magnesium, copper, zinc, manganese, chloride, potassium, sodium, selenium, chromium, molybdenum, taurine, and L-carnitine. Minerals are usually added in salt form. The presence and amounts of specific minerals and other vitamins will vary depending on the intended infant population.

If necessary, the infant formula may contain emulsifiers and stabilisers such as soy lecithin, citric acid esters of mono- and di-glycerides, and the like.

The infant formula may optionally contain other substances which may have a beneficial effect such as fibres, lactoferrin, nucleotides, nucleosides, and the like.

Finally, the formula will contain a probiotic bacterial strain 10e3 to 10e12 cfu/g infant formula, more preferably 10e6 to 10e9 cfu/g formula.

The infant formula described above may be prepared in any suitable manner. For example, they may be prepared by blending together the protein, the carbohydrate source, and the fat source in appropriate proportions. If used, the emulsifiers may be included at this point. The vitamins and minerals may be added at this point but are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture. The temperature of the water is conveniently about 50° C. to about 80° C. to aid dispersal of the ingredients. Commercially available liquefiers may be used to form the liquid mixture. The liquid mixture is then homogenised; for example in two stages.

The liquid mixture may then be thermally treated to reduce bacterial loads, by rapidly heating the liquid mixture to a temperature in the range of about 80° C. to about 150° C. for about 5 seconds to about 5 minutes, for example. This may be carried out by steam injection, autoclave or by heat exchanger; for example a plate heat exchanger.

Then, the liquid mixture may be cooled to about 60° C. to about 85° C.; for example by flash cooling. The liquid mixture may then be again homogenised; for example in two stages at about 10 MPa to about 30 MPa in the first stage and about 2 MPa to about 10 MPa in the second stage. The homogenised mixture may then be further cooled to add any heat sensitive components; such as vitamins and minerals. The pH and solids content of the homogenised mixture are conveniently adjusted at this point.

The homogenised mixture is transferred to a suitable drying apparatus such as a spray drier or freeze drier and converted to powder. The powder should have a moisture content of less than about 5% by weight. The probiotic bacterial strain may be added at this stage by dry-mixing.

In another embodiment, the composition may be a supplement including the probiotic bacterial strain in an amount sufficient to achieve the desired effect in an individual. This form of administration is more suited to children although the probiotic may be administered to infants in the form of drops of oil in which the probiotic bacteria are suspended. An example of such a product is BioGaia Probiotic drops containing L. reuteri DSM 17938 sold by BioGaia AB, Sweden.

Preferably the daily dose of the probiotic is from 10e3 to 10e12 cfu. The amount of probiotic to be included in the supplement will be selected accordingly depending upon how the supplement is to be administered. For example, if the supplement is to be administered twice a day, each supplement may contain 5×10e2 to 5×10e11 cfu of probiotic. The supplement may be in the form of tablets, capsules, pastilles, suppositories, gums or a liquid for example. The supplement may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellifying agents and gel forming agents. The supplement may also contain conventional pharmaceutical additives and adjuvants, excipients and diluents, including, but not limited to, water, gelatine of any origin, vegetable gums, ligninsulfonate, talc, sugars, starch, gum arabic, vegetable oils, polyalkylene glycols, flavouring agents, preservatives, stabilizers, emulsifying agents, buffers, lubricants, colorants, wetting agents, fillers, and the like.

Further, the supplement may contain an organic or inorganic carrier material suitable for oral or enteral administration as well as vitamins, minerals trace elements and other micronutrients in accordance with the recommendations of Government bodies such as the USRDA.

In one embodiment the invention relates to the reduction of sleep disturbances and/or improving sleep patterns in humans in adults, older children (in particular children between 3 and 12), adolescents or at any age.

In another embodiment the invention relates to deliver the described benefits by the use of probiotics to pets and other animals, such as cats, dogs or horses The invention will now be further illustrated by reference to the following examples:—

Example 1

An example of the composition of an infant formula for use according to the present invention is given below. This composition is given by way of illustration only. The proteins of the below composition are from whey and casein (for example 70% whey and 30% casein). In an alternative, the proteins are from whey only.

| Nutrient | per 100 kcal | per liter |
|---|---|---|
| Energy (kcal) | 100 | 670 |
| Protein (g) | 1.83 | 12.3 |
| Fat (g) | 5.3 | 35.7 |
| Linoleic acid (g) | 0.79 | 5.3 |
| α-Linolenic acid (mg) | 101 | 675 |
| Lactose (g) | 11.2 | 74.7 |
| Prebiotic (100% GOS) (g) | 0.64 | 4.3 |
| Minerals (g) | 0.37 | 2.5 |
| Na (mg) | 23 | 150 |
| K (mg) | 89 | 590 |
| Cl (mg) | 64 | 430 |
| Ca (mg) | 62 | 410 |
| P (mg) | 31 | 210 |
| Mg (mg) | 7 | 50 |
| Mn (μg) | 8 | 50 |
| Se (μg) | 2 | 13 |
| Vitamin A (RE) | 105 | 700 |
| Vitamin D (μg) | 1.5 | 10 |
| Vitamin E (mg TE) | 0.8 | 5.4 |
| Vitamin K1 (μg) | 8 | 54 |
| Vitamin C (mg) | 10 | 67 |
| Vitamin B1 (mg) | 0.07 | 0.47 |
| Vitamin B2 (mg) | 0.15 | 1.0 |
| Niacin (mg) | 1 | 6.7 |
| Vitamin B6 (mg) | 0.075 | 0.50 |
| Folic acid (μg) | 9 | 60 |
| Pantothenic acid (mg) | 0.45 | 3 |
| Vitamin B12 (μg) | 0.3 | 2 |

-continued

| Nutrient | per 100 kcal | per liter |
|---|---|---|
| Biotin (µg) | 2.2 | 15 |
| Choline (mg) | 10 | 67 |
| Fe (mg) | 1.2 | 8 |
| I (µg) | 15 | 100 |
| Cu (mg) | 0.06 | 0.4 |
| Zn (mg) | 0.75 | 5 |
| *Lactobacillus reuteri* DSM 17938 | $2.10^7$ cfu/g of powder | |

Example 2

An example of the composition of a follow up infant formula for use according to the present invention is given below. This composition is given by way of illustration only. The proteins of the below composition are from whey and casein. In an alternative, the proteins are from whey only.

| | Follow up infant formula For infants 6 to 12 months | |
|---|---|---|
| Nutrient | per 100 kcal | per liter |
| Energy (kcal) | 100 | 630 |
| Protein (g) | 1.8 | 11.3 |
| Fat (g) | 5.0 | 31.5 |
| Linoleic acid (g) | 0.75 | 4.7 |
| α-Linolenic acid (mg) | 95 | 600 |
| Lactose (g) | 11.9 | 75 |
| Prebiotic (100% GOS) (g) | 0.63 | 4.0 |
| Minerals (g) | 0.37 | 2.3 |
| Na (mg) | 25 | 158 |
| K (mg) | 80 | 504 |
| Cl (mg) | 65 | 410 |
| Ca (mg) | 60 | 378 |
| P (mg) | 33 | 208 |
| Mg (mg) | 7 | 44 |
| Mn (µg) | 5 | 32 |
| Se (µg) | 3 | 19 |
| Vitamin A (µg RE) | 90 | 570 |
| Vitamin D (µm) | 1.5 | 9.5 |
| Vitamin E (mg TE) | 0.8 | 5.0 |
| Vitamin K1 (µm) | 8 | 50 |
| Vitamin C (mg) | 15 | 95 |
| Vitamin B1 (mg) | 0.1 | 0.6 |
| Vitamin B2 (mg) | 0.1 | 0.6 |
| Niacin (mg) | 0.5 | 3.2 |
| Vitamin B6 (mg) | 0.06 | 0.4 |
| Folic acid (µg) | 15 | 95 |
| Pantothenic acid (mg) | 0.8 | 5.0 |
| Vitamin B12 (µg) | 0.2 | 1.3 |
| Biotin (µg) | 2.0 | 12.6 |
| Choline (mg) | 15 | 95 |
| Fe (mg) | 1.0 | 6.3 |
| I (µg) | 15 | 95 |
| Cu (mg) | 0.06 | 0.4 |
| Zn (mg) | 0.9 | 5.7 |
| BB536 (=ATCC BAA-999, deposited by Morinaga, (sourced from Morinaga Milk Industry, Co., Ltd, Tokyo, Japan) | $2.10^6$ cfu/g of powder | |
| AND/OR | AND/OR | |
| *Lactobacillus reuteri* DSM 17938 (sourced from Biogaia-BioGaia AB, Sweden) | $10^7$ cfu/g of powder | |

Example 3

An example of the composition of a follow up infant formula for use according to the present invention is given below. This composition is given by way of illustration only. The proteins of the below composition are from whey and casein in a ratio of 50/50. In an alternative, the proteins are from whey only or 70% (w/w) from whey. In the below example 16% (w/w) of the carbohydrates are rice carbohydrates (in a similar alternative example 25% of the carbohydrates are rice carbohydrates). Prebiotics can be added (e.g. GOS, 0.5 g/100 kcal) to the formulation.

| | Follow up infant formula For infants 6 to 12 months | |
|---|---|---|
| Nutrient | per 100 kcal | per liter |
| Energy (kcal) | 100 | 670 |
| Protein (g) | 2.2 | 14.6 |
| Fat (g) | 3.7 | 31.6 |
| Linoleic acid (g) | 0.76 | 5.1 |
| α-Linolenic acid (mg) | 88 | 590 |
| Lactose (g) | 7.44 | 81.2 |
| Maltodextrine (g) | 2.1 | 14.2 |
| Starch (g) | 2.59 | 17.3 |
| Prebiotic (100% GOS) (g) | 0.63 | 4.0 |
| Minerals (g) | 0.58 | 3.9 |
| Na (mg) | 39 | 158 |
| K (mg) | 113 | 760 |
| Cl (mg) | 73 | 490 |
| Ca (mg) | 105 | 700 |
| P (mg) | 66 | 440 |
| Mg (mg) | 11.4 | 76 |
| Vitamin A (µg RE) | 90 | 570 |
| Vitamin D (µg) | 1.5 | 9.5 |
| Vitamin E (mg TE) | 0.8 | 5.0 |
| Vitamin K1 (µm) | 8 | 50 |
| Vitamin C (mg) | 15 | 95 |
| Vitamin B1 (mg) | 0.1 | 0.6 |
| Vitamin B2 (mg) | 0.1 | 0.6 |
| Niacin (mg) | 0.5 | 3.2 |
| Vitamin B6 (mg) | 0.06 | 0.4 |
| Folic acid (µg) | 15 | 95 |
| Pantothenic acid (mg) | 0.8 | 5.0 |
| Vitamin B12 (µg) | 0.2 | 1.3 |
| Biotin (µg) | 2.0 | 12.6 |
| Choline (mg) | 15 | 95 |
| Fe (mg) | 1.0 | 6.3 |
| I (µg) | 15 | 95 |
| Cu (mg) | 0.06 | 0.4 |
| Zn (mg) | 0.9 | 5.7 |
| *Lactobacillus reuteri* DSM 17938 (sourced from Biogaia-BioGaia AB, Sweden) | $10^7$ cfu/g of powder | |
| AND/OR | AND/OR | |
| *Lactobacillus rhamnosus* CGMCC 1.3724 | $10^6$ cfu/g of powder | |
| AND/OR | AND/OR | |
| BB536 (=ATCC BAA-999, deposited by Morinaga, (sourced from Morinaga Milk Industry, Co., Ltd, Tokyo, Japan) | $10^6$ cfu/g of powder | |

Example 4

Effect of Probiotics on Sleep Quality

Stress administered to pregnant rats leads to sleep quality alterations in the progeny (i.e. prenatal stress or PRS animals) similar to those experienced by infants and children with perturbed sleep patterns and by adults suffering from poor sleep quality and insomnia. These alterations are characterized by a lighter sleep and increased wake up episodes (i.e. increased amounts of REM sleep, decreased amounts of NREM, and increased sleep fragmentation (Dugovic, 1999)). This model has been used to test the efficacy of probiotic administration on sleep quality.

PRS (i.e. progeny from dams submitted to restrain stress during pregnancy) and control (i.e. progeny from undisturbed dams) rats were implanted under deep anaesthesia with chronic electrodes for polygraphic recordings of frontoparietal electroencephalogram (EEG), electrooculogram (EOG), and nuchal electromyogram (EMG). All electrodes were attached to a microconnector and fixed to the skull with dental cement. EEG, EOG, and EMG activities were recorded on a polygraph (EEG-4414 A/K; Nihon-Khoden) with an output connected to a computer for on-line spectral analysis of the EEG. After surgery for electrode implantation, the rats were individually housed in Plexiglas cages (30 cm diameter, 40 cm high), and left undisturbed for 2 weeks. The animals were then habituated to the sleep recording procedure for the next 14 d. They received placebo or one of two probiotics by gavage during this time. At the end of the habituation period, sleep was recorded for a period of 24 hr, beginning at the onset of the light phase. Polygraphic recordings were visually scored by 30 sec epochs. Those epochs are classified as being wake, NREM sleep, or REM sleep. The amount of time spent in the three vigilance states and the number and duration of episodes for each state were recorded. The following groups were studied:

PRSr: PRS animals that received 1 ml/day of oil drops containing $10^9$ cfu *Lactobacillus reuteri* DSM 17938 (BioGaia Probiotic drops, BioGaia AB, Sweden)

PRSb: PRS animals that received 1 ml/day of saline solution containing $10^{10}$ cfu *Bifidobacterium longum* NCC3001 (ATCC BAA-999, initially provided by Morinaga Milk Industry Co. Ltd) dissolved in saline PRSp: PRS animals that received 1 ml/day of drops containing the same oil carrier as the *L. reuteri* product but without the probiotic.

Control: control animals that received 1 ml/day of drops containing the same oil carrier as the *L. reuteri* product but without the probiotic.

Results are shown in FIGS. 1 and 2. As expected, compared to the Control group, the amount of time spent in quiet sleep (NREM, FIG. 1B) was reduced and the time spent in active sleep (REM, FIG. 1C) was increased in PRSp animals, whereas the duration of the wake state (FIG. 1A) was similar in both groups. The administration of both probiotics normalized the duration of NREM and REM states without affecting the duration of the wake state. Consistently, the number of episodes over 24 hours of wake (FIG. 2A), NREM (FIG. 2B) and REM (FIG. 2C) states was higher in PRSp than in Control animals, which indicates increased sleep fragmentation and higher number of wake up episodes in the PRSp group. Both probiotics reduced the number of wake up episodes and sleep fragmentation to Control levels.

In conclusion, the data indicate that probiotic administration normalizes the sleep patterns and improves sleep quality in the animal model. Better sleep quality likely resulted in improved alertness during the wake state in the probiotic groups, as suggested by the lower number and the increased duration (data not shown) of the wake episodes in the probiotic groups compared to the placebo PRS group.

The invention claimed is:

1. A method for reducing stress-induced sleep disturbances comprising administering a therapeutically-effective amount of a composition including a probiotic bacterial strain that is *Lactobacillus reuteri* DSM 17938 to a human or animal having a low level of brain-derived neurotrophic factor (BDNF).

2. The method of claim 1 wherein the human or animal is selected from the group consisting of infants, young animals and young children.

3. The method of claim 1, wherein the human or animal suffers from poor quality sleep and/or insomnia.

4. The method of claim 1, wherein the composition induces a mature sleep pattern or reduces the number of episodes of wakefulness in the human or animal.

5. The method of claim 1, wherein the daily dose of probiotic bacteria is from $10^3$ to $10^{12}$ colony forming units (cfu).

6. The method of claim 1, wherein the composition comprises from $10^3$ to $10^{12}$ colony forming units (cfu) of probiotic bacteria per g of composition.

7. The method of claim 1, wherein the composition is a supplement and the probiotic bacterial strain is present in an amount of from $10^3$ to $10^{12}$ cfu per unit dose.

8. The method of claim 1, wherein the composition is in a form selected from the group consisting of a human milk fortifier, an infant formula, a follow on formula, a growing up milk, an infant cereal, a baby food, a yogurt, a cereal bar, a breakfast cereal, a dessert, a frozen food, a soup, a pet food, a liquid suspension, a powder, a tablet, a gum, a candy, a nutritional composition, and a nutritional supplement.

9. The method of claim 1, wherein the composition induces a more mature sleep pattern.

10. The method of claim 1, wherein the composition comprises carbohydrates, and the carbohydrates comprise rice carbohydrates.

11. The method of claim 1, wherein the composition is a starter infant formula or a follow-up infant formula.

12. A method for improving sleep quality or sleep patterns comprising administering a therapeutically-effective amount of a composition comprising a probiotic bacterial strain that is *Lactobacillus reuteri* DSM 17938 to a human or animal having a low level of brain-derived neurotrophic factor (BDNF).

13. The method of claim 12 wherein the human or animal is selected from the group consisting of infants, young animals and young children.

14. The method of claim 12, wherein the human or animal suffers from poor quality sleep and/or insomnia.

15. The method of claim 12, wherein the composition induces a mature sleep pattern or reduces the number of episodes of wakefulness in the human or animal.

16. The method of claim 12, wherein the daily dose of probiotic bacteria is from $10^3$ to $10^{12}$ colony forming units (cfu).

17. The method of claim 12, wherein the composition comprises from $10^3$ to $10^{12}$ colony forming units (cfu) of probiotic bacteria per g of composition.

18. The method of claim 14, wherein the poor quality sleep and/or insomnia is stress-induced.

19. The method of claim 12, wherein the composition is a supplement and the probiotic bacterial strain is present in an amount of from $10^3$ to $10^{12}$ cfu per unit dose.

20. The method of claim 12, wherein the composition is in a form selected from the group consisting of a human milk fortifier, an infant formula, a follow on formula, a growing up milk, an infant cereal, a baby food, a yogurt, a cereal bar, a breakfast cereal, a dessert, a frozen food, a soup, a pet food, a liquid suspension, a powder, a tablet, a gum, a candy, a nutritional composition, and a nutritional supplement.

21. The method of claim 12, wherein the composition induces a more mature sleep pattern.

22. The method of claim 12, wherein the composition comprises carbohydrates, and the carbohydrates comprise rice carbohydrates.

23. The method of claim 12, wherein the composition is a starter infant formula or a follow-up infant formula.

24. A method for reducing stress-induced sleep disturbances comprising administering a therapeutically-effective amount of a composition including a probiotic bacterial strain that is *Bifidobacterium longum* BAA-999 to a human or animal having a low level of brain-derived neurotrophic factor (BDNF).

* * * * *